United States Patent

Witte et al.

[11] 3,947,446
[45] Mar. 30, 1976

[54] NOVEL 1-[3-(5,6,7,8-TETRAHYDRONAPHTH-1-YLOXY)-PROPYL]-PIPERAZINE COMPOUNDS AND THERAPEUTIC COMPOSITIONS

[75] Inventors: Ernst-Christian Witte, Mannheim; Kurt Stach, Mannheim-Waldhof; Karl Dietmann, Mannheim-Vogelstang; Gisbert Sponer, Mannheim-Waldhof, all of Germany

[73] Assignee: Boehringer Mannheim GmbH, Mannheim-Waldhof, Germany

[22] Filed: June 14, 1973

[21] Appl. No.: 370,068

[30] Foreign Application Priority Data
July 20, 1972 Germany............................ 2235597

[52] U.S. Cl. ........ 260/268 BC; 260/348 R; 424/250
[51] Int. Cl.[2].................................. C07D 295/12
[58] Field of Search............................ 260/268 BC

[56] References Cited
OTHER PUBLICATIONS
Pollard et al., J. Org. Chem., pp. 1935–1937, (1958).
Cassella Farbwerke Mainkur A–G by Adolf Stachel, Chemical Abstracts, Vol. 63, pp. 617–618, (1965).
Cronenberger et al., Chemical Abstracts, Vol. 66, 85761J, (1967).

Primary Examiner—Raymond V. Rush
Assistant Examiner—Jose Tovar
Attorney, Agent, or Firm—Burgess, Dinklage & Sprung

[57] ABSTRACT
1-[3-(5,6,7,8-tetrahydronaphth-1-yloxy)-propyl]-piperazine derivatives of the formula

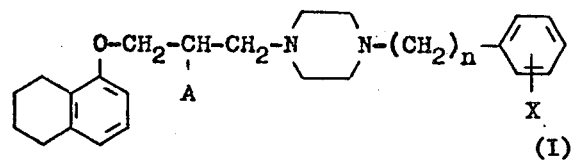

(I)

wherein
A is hydrogen or hydroxyl;
X is hydrogen or halogen or alkyl, alkoxy, alkylthio, trifluoromethyl, hydroxyl, nitro, amino, acylamino (i.e., alkanoylamino) or alkylsulfonylamino; and
$n$ is 0, 1 or 2;
and the pharmacologically compatible salts thereof; exhibit outstanding blood pressure depressing activity, i.e., possess antihypertensive properties.

16 Claims, No Drawings

NOVEL 1-[3-(5,6,7,8-TETRAHYDRONAPHTH-1-YLOXY)-PROPYL]-PIPERAZINE COMPOUNDS AND THERAPEUTIC COMPOSITIONS

The present invention is concerned with 1-[3-(5,6,7,8-tetrahydronaphth-1-yloxy)-propyl]-piperazine compounds and with the therapeutic compositions containing them.

The 1-[3-(5,6,7,8-tetrahydronaphth-1-yloxy)-propyl]-piperazine derivatives according to the present invention are compounds of the formula:

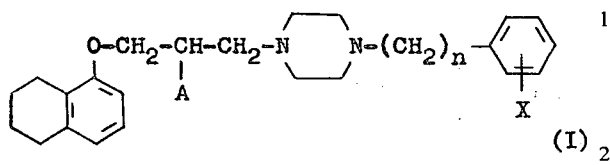

wherein
A is hydrogen or hydroxyl;
X is hydrogen or halogen or alkyl, alkoxy, alkylthio, trifluoromethyl, hydroxyl, nitro, amino, acylamino (i.e., alkanoylamino) or alkylsulfonylamino; and
$n$ is 0, 1 or 2;
and the pharmacologically compatible salts thereof.

The new compounds according to the present invention possess an outstanding blood pressure-sinking action and thus have anti-hypertensive properties. Furthermore, in rats they inhibit the anaphylactoid reactions released by dextran.

The alkyl, alkoxy, alkylthio, acylamino and alkylsulfonylamino radicals in the new compounds of general formula (I) generally contain up to 6 carbon atoms and preferably contain up to 3 carbon atoms.

The new compounds according to the present invention can be prepared, for example, by one of the following methods:

a. reaction of a compound of the general formula:

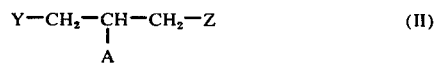

wherein A has the same meaning as above and Y and Z are reactive groups, which can be the same or different, with 5,6,7,8-tetrahydro-1-naphthol and a piperazine of the general formula:

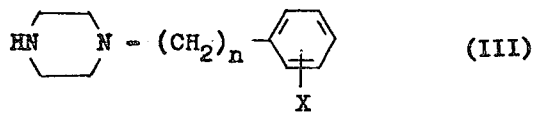

wherein X and $n$ have the same meanings as above, optionally with intermediate protection of the group A; or b. when A is a hydroxyl group, reaction of a compound of the general formula:

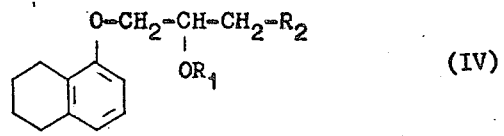

wherein $R_1$ is a hydrogen atom and $R_2$ is a halogen atom or $R_1$ and $R_2$ together represent a valency bond, with a piperazine of general formula (III), whereafter, if desired, the residue X is subsequently converted into a different residue X and the compounds obtained are, if desired, converted into pharmacologically compatible salts.

In the case of method (a), all 3 components can, if desired, be reacted together simultaneously. Preferably, however, the reaction is carried out in two steps: first, 5,6,7,8-tetrahydro-1-naphthol is reacted with a compound (II) and the condensation product obtained is then condensed with the compound (III) or the compounds (II) and (III) are first condensed and the product obtained subsequently reacted with 5,6,7,8-tetrahydro-1-naphthol.

These condensation reactions are carried out in the presence of an acid-binding agent, for example of a tertiary amine, such as triethylamine, or of an alkali metal carbonate or bicarbonate, or there is used the sodium or potassium salt of 5,6,7,8-tetrahydro-1-naphthol, which can be obtained in known manner. As solvent, there can be used, for example, a lower ketone, for example methyl ethyl ketone, or a lower alcohol, for example isopropanol, or tetrahydrofuran. When A signifies a hydroxyl group, it is preferable temporarily to block this by a protective group which can easily be split off, for example an acyl radical or a benzyl, triphenyl-methyl or tetrahydropyranyl-(2) radical. These protective groups can subsequently be again removed by acidic or alkaline hydrolysis or hydrogenolytically.

The reactive groups Y and Z in the compounds of general formula (II) are preferably acid residues, for example of hydrohalic or sulfonic acids.

The reaction according to method (b) can be carried out by mixing molar amounts of the reaction components and leaving the mixture to stand at ambient temperature; by briefly heating, optionally in a pressure vessel, the reaction can be accelerated and, if desired, a solvent, for example a lower alcohol, can be added thereto.

If desired, the residues X can, after the condensation according to method (a) or (b), be converted into a different residue X; for example, a nitro group can be reduced to an amino group or an amino group can be acylated.

For the preparation of salts, the compounds (I) according to the present invention are reacted with pharmacologically compatible organic or inorganic acids, for example with hydrochloric acid, sulfuric acid, phosphoric acid, lactic acid, citric acid or an alkyl-sulfonic acid.

The following Examples are given for the purpose of illustrating the preparation of compounds of the present invention:

EXAMPLE 1

Preparation of 4-(4-Chlorophenyl)-1-[3-(5,6,7,8-tetrahydronaphth-1-yloxy)-prop-1-yl]-piperazine 53.2 g. (0.385 mole) powdered, dry potassium carbonate were added, with stirring, over the course of 3 hours to a boiling mixture of 51.8 g. (0.35 mole) 5,6,7,8-tetrahydro-1-naphthol, 350 ml. anhydrous methyl ethyl ketone and 212.0 g. (1.05 mole) 1,3-dibromopropane. Subsequently, the reaction mixture was boiled under reflux for a further 6 hours, then filtered with suction and the filter cake washed with acetone. The combined organic filtrates were evaporated in a vacuum, the evaporation residue was taken up in chloroform and the chloroform solution was extracted several times with a dilute aqueous solution of sodium hydroxide, then washed neutral with water and dried. The chloroform was evaporated off and the residue, which was an oil of low viscosity, was distilled at oil pump vacuum. Between 125° and 135°C./0.05 mm.Hg., there were obtained 33.1 g. of 1-(5,6,7,8-tetrahydronaphth-1-yloxy)-3-bromopropane. The yield was 35% of theory, which corresponded to a yield of 77.5%, calculated from the amount of reacted tetrahydro-1-naphthol; $n_D^{20} = 1.5626$.

A mixture of 8.9 g. (33 mMole) 1-(5,6,7,8-tetrahydronaphth-1-yloxy)-3-bromopropane, 6.5 g. (33 mMole) 1-(4-chlorophenyl)-piperazine, 4.20 g. (50 mMole) sodium bicarbonate and 35 ml. anhydrous alcohol were heated under reflux for 18 hours and the reaction mixture then evaporated in a vacuum. The evaporation residue was stirred with 1N aqueous sodium hydroxide solution and the undissolved material was filtered off with suction, washed with water, dried and recrystallized from alcohol, with the addition of charcoal. There were obtained 7.1 g. (56% of theory) colorless 4-(4-chlorophenyl)-1-[3-(5,6,7,8-tetrahydronaphth-1-yloxy)-prop-1-yl]-piperazine, which has a melting point of 97°C. The dihydrochloride obtained herefrom in the usual manner melts, with decomposition, at 200°–203°C.

EXAMPLE 2

Preparation of
4-(2-Chlorophenyl)-1-[3-(5,6,7,8-tetrahydronaphth-1-yloxy)-prop-1-yl]-piperazine A mixture of 10.7 g. (40 mMole) 1-(5,6,7,8-tetrahydronaphth-1-yloxy)-3-bromopropane (prepared in the manner described in Example 1), 7.9 g. (40 mMole) 2-chlorophenyl-piperazine, 8.1 g. (80 mMole) anhydrous triethylamine and 40 ml. anhydrous tetrahydrofuran was stirred at reflux temperature for 24 hours. After cooling, the reaction mixture was filtered with suction, the precipitate was washed with tetrahydrofuran and the combined filtrates obtained were evaporated in a vacuum. The evaporation residue was taken up in chloroform, washed twice with 0.5N aqueous sodium hydroxide solution and twice with an aqueous solution of sodium chloride and then dried over anhydrous sodium sulfate. After evaporation in a vacuum, there was obtained a non-crystallizing oil which was dissolved in warm isopropanol. After filtering, hydrogen chloride-containing dioxan was added to the filtrate to precipitate out 13.4 g. (80% of theory) 4-(2-chlorophenyl)-1-[3-(5,6,7,8-tetrahydronaphth-1-yloxy)-prop-1-yl]-piperazine hydrochloride, which has a melting point of 228°–230°C.

The following compounds were obtained in an analogous manner:
4-(2-methylthiophenyl)-1-[3-(5,6,7,8-tetrahydronaphth-1-yloxy)-prop-1-yl]-piperazine from 1-(5,6,7,8-tetrahydronaphth-1-yloxy)-3-bromopropane and 1-(2-methylthiophenyl)-piperazine; yield 64% of theory; m.p. of the hydrochloride 224°–225°C. decomp.); 4-(3-trifluoromethylphenyl)-1-[3-(5,6,7,8-tetrahydronaphth-1-yloxy)-prop-1-yl]-piperazine from 1-(5,6,7,8-tetrahydro-napth-1-yloxy)-3-bromopropane and 1-(3-trifluoromethylphenyl)-piperazine; yield 84% of theory; m.p. of the dihydrochloride: 182°–183°C.

EXAMPLE 3

Preparation of
4-(2-Methylphenyl)-1-[3-(5,6,7,8-tetrahydronaphth-1-yloxy)-prop-1-yl]-piperazine 40.4 g. (0.4 mole) triethylamine and 31.5 g. (0.2 mole) 1-chloro-3-bromopropane were added to a solution of 35.3 g. (0.2 mole) 1-(2-methylphenyl)-piperazine in 100 ml. anhydrous tetrahydrofuran and the reaction mixture then heated under reflux for 14 hours. After cooling, the reaction mixture was mixed with 10 ml. anhydrous ether, the crystals which separate out were filtered off with suction and the filtrate was evaporated in a vacuum. 46.2 g. of an oily substance remained behind which consisted of crude 4-(2-methylphenyl)-1-(3-chloropropyl)-piperazine; the corresponding hydrochloride decomposes between 185° and 210°C.

A mixture of 8.15 g. (55 mMole) 5,6,7,8-tetrahydro-1-naphthol, 7.60 g. (55 mMole) powdered dry potassium carbonate and 100 ml. anhydrous methyl ethyl ketone was heated under reflux for 2 hours and then cooled somewhat. 0.2 g. potassium iodide were added thereto and a solution of 12.64 g. (50 mMole) 4-(2-methylphenyl)-1-(3-chloropropyl)-piperazine in 50 ml. anhydrous methyl ethyl ketone then added dropwise, whereafter the reaction mixture was heated under reflux for a further 16 hours. After filtering with suction, the filter cake obtained was washed with acetone. The combined organic filtrates were evaporated in a vacuum, the oily evaporation residue was taken up in chloroform and the chloroform solution was extracted several times with a dilute aqueous solution of sodium hydroxide and then with distilled water. After drying and evaporating in a vacuum, there was obtained an oily product which was dissolved in ether and treated with dry hydrogen chloride. The precipitated 4-(2-methylphenyl)-1-[3-(5,6,7,8-tetrahydronaphth-1-yloxy)-prop1 -yl]-piperazine hydrochloride thus obtained was filtered off with suction, washed with some ether and finally with alcohol to which some concentrated hydrochloric acid had been added. The yield was 72% of theory and the product has a melting point of 243°–244°C.

The following compounds were obtained in an analogous manner:
1-[3-(5,6,7,8-tetrahydronaphth-1-yloxy)-propyl]-4-phenyl-piperazine from 5,6,7,8-tetrahydro-1-naphthol and 1-(3-chloropropyl)-4-phenyl-piperazine; yield 72% of theory; m.p. of the dihydrochloride 210°–211°C. (decomp.);
1-[3-(5,6,7,8-tetrahydronaphth-1-yloxy)-propyl]-4-(2-methoxyphenyl)-piperazine from 5,6,7,8-tetrahydro-1-naphthol and 1-(3-chloropropyl)-4-(2-methoxyphenyl)-piperazine; yield 48% of theory; m.p. of the dihydrochloride 202°–203°C. (decomp.).

EXAMPLE 4

Preparation of 1-[3-(5,6,7,8-tetrahydronaphth-1-yloxy)-2-hydroxyprop-1-yl]-4-(2-methoxyphenyl)-piperazine A mixture of 11.24 g. (55 mMole) 1-(5,6,7,8-tetrahydronaphth-1-yloxy)-2,3-epoxypropane and 9.62 g. (50 mMole) 1-(2-methoxyphenyl)-piperazine was stirred for 5 hours in an oil bath at a bath temperature of 120°C. Subsequently, the reaction mixture was dissolved in 350 ml. hot isopropanol, cooled and the precipitated crystals filtered off with suction. After repeated recrystallization from isopropanol, there were obtained 12.8 g. (64% of theory) pure 1-[3-(5,6,7,8-tetrahydronaphth-1-yloxy)-2-hydroxyprop-1-yl]-4-(2-methoxyphenyl)-piperazine, which has a melting point of 123°-124°C. The dihydrochloride melted, with decomposition, at 212°-213°C.

The epoxide used as starting material was prepared in the following manner:

A solution of 10.0 g. (0.25 mole) sodium hydroxide in 34 ml. water was added dropwise to a mixture, heated to 72°C., of 37.1 g. (0.25 mole) 5,6,7,8-tetrahydro-1-naphthol and 46.2 g. (0.5 mole) epichlorhydrin, the temperature being maintained between 72° and 75°C. by occasional cooling. Subsequently, the reaction mixture was maintained for 2.5 hours at 75° C. After cooling and the addition of 50 ml. water, it was extracted several times with chloroform and the combined chloroform extracts were washed with distilled water, dried over anhydrous sodium sulfate and then freed from chloroform in a vacuum. The oily residue obtained was distilled. Between 124° and 128°C./0.3 mm.Hg., there were obtained 40.4 g. (79% of theory) 1-(5,6,7,8-tetrahydronaphth-1-yloxy-2,3-epoxypropane.

The following compounds were obtained in an analogous manner:

1-[3-(5,6,7,8-tetrahydronaphth-1-yloxy)-2-hydroxyprop-1-yl]-4-phenyl-piperazine from 1-(5,6,7,8-tetrahydronaphth1-yloxy)-2,3-epoxypropane and 1-phenyl-piperazine; yield 68% of theory; m.p. of the dihydrochloride 213°-214°C. (decomp.);

1-[3-(5,6,7,8-tetrahydronaphth-1-yloxy)-2-hydroxyprop-1-yl]-4-(2-methylphenyl)-piperazine from 1-(5,6,7,8-tetrahydronaphth-1-yloxy)-2,3-epoxypropane and 1-(2-methyl-phenyl)-piperazine; yield 73% of theory; m.p. of the dihydrochloride 202°-204°C.;

1-[3-(5,6,7,8-tetrahydronaphth-1-yloxy)-2-hydroxyprop-1-yl]-4-(2-chlorophenyl)-piperazine from 1-(5,6,7,8-tetrahydronaphth-1-yloxy)-2,3-epoxypropane and 1-(2-chlorophenyl)-piperazine; yield 87% of theory; m.p. 90°-91°C. (recrystallized from isopropanol); m.p. of the hydrochloride 132°-133°C.;

1-[3-(5,6,7,8-tetrahydronaphth-1-yloxy)-2-hydroxyprop-1-yl]-4-(3-methoxyphenyl)-piperazine from 1-(5,6,7,8-tetrahydronaphth-1-yloxy)-2,3-epoxypropane and 1-(3-methoxyphenyl)-piperazine; yield 76% of theory; m.p. of the dihydrochloride 208°C. (decomp.);

1-[3-(5,6,7,8-tetrahydronaphth-1-yloxy)-2-hydroxyprop-1-yl]-4-(4-methoxyphenyl)-piperazine from 1-(5,6,7,8-tetrahydronaphth-1-yloxy)-2,3-epoxypropane and 1-(4-(methoxyphenyl)-piperazine; yield 72% of theory; m.p. 83°-84°C. (recrystallized from isopropanol); m.p. of the dihydrochloride 230°-231°C. (decomp.).

EXAMPLE 5

Preparation of
1-[3-(5,6,7,8-tetrahydronaphth-1-yloxy)-2-hydroxyprop-1-yl]-4-(2-methylthiophenyl)-piperazine.

A mixture of 10.2 g. (50 mMole) 1-(5,6,7,8-tetrahydronaphth-1-yloxy)-2,3-epoxypropane and 10.4 g. (50 mMole) 1-(2-methylthiophenyl)-piperazine was left to stand for 24 hours in a closed vessel and then brought to crystallization by the addition of ligroin. After filtering off with suction, there were obtained 19.8 g. (96% of theory) 1-[3-(5,6,7,8-tetrahydronaphth-1-yloxy)-2-hydroxyprop-1-yl]-4-(2-methylthiophenylpiperazine which was recrystallized from 300 ml. of a mixture of ligroin and ethyl acetate (4:6 v/v). The yield was 15.6 g. (76% of theory); m.p. 120°-121°C.

The following compounds were obtained in an analogous manner:

1-[3-(5,6,7,8-tetrahydronaphth-1-yloxy)-2-hydroxyprop-1-yl]-4(3-trifluoromethylphenyl)-piperazine from 1-(5,6,7,8-tetrahydronaphth-1-yloxy)-2,3-epoxypropane and 1-(3-trifluoromethylphenyl)piperazine; yielded 74% of theory; m.p. 104°-105°C. (recrystallized from ligroin and ethyl acetate (8:2 v/v));

1-[3-(5,6,7,8-tetrahydronaphth-1-yloxy)-2-hydroxyprop-1-yl]-4-(4-chlorophenyl)-piperazine from 1-(5,6,7,8-tetrahydronaphth-1-yloxy)-2,3-epoxypropane and 1-(4-chlorophenyl)-piperazine; yielded 67% of theory; m.p. 94°C. (recrystallized from ethyl acetate and ligroin (2:8 v/v));

1-[3-(5,6,7,8-tetrahydronaphth-1-yloxy)-2-hydroxyprop-1-yl]-4-benzyl-piperazine from 1-(5,6,7,8-tetrahydronaphth-1-yloxy)-2,3-epoxypropane and 1-benzyl-piperazine; yield 64% of theory; m.p. of the hydrochloride 236°-237°C.

EXAMPLE 6

Preparation of
1-[3-(5,6,7,8-Tetrahydronaphth-1-yloxy)-prop-1-yl]-4-(2-nitrophenyl)-piperazine A mixture of 75.0 g. (0.29 mole) 1-(5,6,7,8-tetrahydronaphth-1-yloxy)-3-bromopropane (prepared in the manner described in Example 1), 60.0 g. (0.29 mole) 1-(o-nitrophenyl)-piperazine, 59 g. (0.58 mole) anhydrous triethylamine and 250 ml. anhydrous tetrahydrofuran was stirred for 28 hours under reflux, then cooled and the precipitated triethylamine hydrobromide was filtered off with suction. The filtrate was evaporated in a vacuum, a viscous, deep red oil remaining behind. For purification, this crude product was dissolved in dioxan, converted into the hydrochloride by passing in gaseous hydrogen chloride and the hydrochloride thus obtained was recrystallized from ethanol. In this manner there was obtained 1-[3-(5,6,7,8-tetrahydronaphth-1-yloxy)-prop-1-yl]-4-(2-nitrophenyl)-piperazine hydrochloride in a yield of 73% of theory; m.p. 214°-215°C.

EXAMPLE 7

Preparation of
1-[3-(5,6,7,8-Tetrahydronaphth-1-yloxy)-prop-1-yl]-4-(2-aminophenyl)-piperazine 22.7 g. (57.5 mMole) 1-[3-(5,6,7,8-tetrahydronaphth-1-yloxy)-prop-1-yl]-4-(2-nitrophenyl)-piperzzine (obtained by the liberation of the base from the hydrochloride obtained according to Example 6 by means of a concentrated aqueous solution of sodium hydroxide) were dissolved in 150 ml. anhydrous tetrahydrofuran, about 20 g. Raney nickle were added thereto, followed by hydrogenation at atmospheric pressure on a shaking device until the theoretical amount of hydrogen had been taken up. After filtering off the catalyst, the filtrate obtained was freed from tetrahydrofuran in a vacuum and the oily residue converted into the hydrochloride by treatment with gaseous hydrogen chloride. In this manner, there was obtained 1-[3-(5,6,7,8-tetrahydronaphth-1-yloxy)-prop- 1-yl]-4-(2-aminophenyl)-piperazine dihydrochloride in a yield of 20.4 g. (89% of theory); m.p. 256°–258°C.

EXAMPLE 8

Preparation of
1-[3-(5,6,7,8-Tetrahydronaphth-1-yloxy)-prop-1-yloxy)-prop-1-yl]-4-(2-acetaminophenyl)-piperazine 6.1 g. (60 mMole) acetic anhydride were added, with stirring, to a solution of 18.3 g. (50 mMole) 1-[3-(5,6,7,8-tetrahydronaphth-1-yloxy)-prop-1-yl]-4-(amino-phenyl)-piperazine (obtained by liberation of the base from the dihydrochloride prepared according to Example 7 by means of a concentrated aqueous solution of sodium hydroxide) in 100 ml. anhydrous pyridine, whereafter the reaction mixture was heated for 1 hour on a steambath. Thereafter, the reaction mixture was substantially evaporated in a vacuum, some water was added to the evaporation residue and then it was left to stand for 1 hour at 30°–35°C. Subsequently, the reaction mixture was extracted several times with ether, the combined ethereal phases were dried over anhydrous sodium sulfate and the ether was finally distilled off. The oily evaporation residue was brought to crystallization by stirring with a very small amount of ether. There were obtained 16.4 g. (80% of theory) 1-[3-(5,6,7,8-tetrahydronaphth-1-yloxy)-prop-1-yl]-4-(2-acetaminophenyl)-piperazine, which has a melting point of 100°–101°C.

EXAMPLE 9

Preparation of
1-[3-(5,6,7,8-Tetrahydronaphth-1-yloxy)-2-hydroxy-prop-1-yl]-4-(2-nitrophenyl)-piperazine 54.4 g. (268 (mMole) 1-(5,6,7,8-tetrahydronaphth-1-yloxy)-2,3-epoxypropane (prepared in the manner described in Example 4) were mixed with 55.5 g. (268 mMole) 1-(o-nitrophenyl)-piperazine and left to stand in a closed vessel for a day. The product was brought to crystallization by the addition of some isopropanol. After recrystallization from 500 ml. isopropanol, there were obtained 88.9 g. (81% of theory) pure 1-[3-(5,6,7,8-tetrahydronaphth-1-yloxy)-2-hydroxyprop-1-yl]-4-(2-nitrophenyl)-piperazine, which has a melting point of 88°–89°C. The hydrochloride thereof, prepared in the usual manner, has a melting point of 186°–187°C.

EXAMPLE 10

Preparation of
1-[3-(5,6,7,8-Tetrahydronaphth-1-yloxy)-2-hydroxy-prop-1-yl]-4-(2-aminophenyl)-piperazine 20.6 g. (50 mMole) 1-[3-(5,6,7,8-tetrahydronaphth-1-yloxy)-2-hydroxy-prop-1-yl]-4-(2-nitrophenyl)-piperazine (prepared in the manner described in Example 9) were hydrogenated in tetrahydrofuran, in the presence of Raney nickel in a manner analogous to that described in Example 7. There were thus obtained 19.4 g. (85% of theory) 1-[3-(5,6,7,8-tetrahydronaphth-1-yloxy)-2-hydroxy-prop-1-yl]-4-(2-aminophenyl)-piperazine dihydrochloride, which has a melting point of 268°–271°C. The free base obtained herefrom in the usual manner melts at 103°–104°C.

EXAMPLE 11

Preparation of
1-[3-(5,6,7,8-Tetrahydronaphth-1-yloxy)-2-hydroxy-prop-1-yl]-4-(2-acetaminophenyl)-piperazine 9.5 g. (25 mMole) 1-[3-(5,6,7,8-tetrahydronaphth-1-yloxy)-2-hydroxy-prop-1-yl]-4-(2-aminophenyl)-piperazine (prepared in the manner described in Example 10) in 50 ml. anhydrous pyridine were acetylated by the addition of 5.1 g. (50 mMole) acetic anhydride and, after treatment with hydrogen chloride, there were obtained 11.6 g. (93% of theory) of a very deliquescent product which commenced to decompose at 70°C. A solution of 11 g. of this hydrochloride in 100 ml. methanol was mixed dropwise with 30 ml. 2N aqueous potassium hydroxide solution, the temperature being kept at 20°C. After leaving to stand overnight, the methanol was distilled off in a vacuum. The residue was mixed with some water, dilute hydrochloric acid was added thereto until the pH was 5 and the oily phase was taken up in isopropanol. By the addition of hydrogen chloridecontaining ether, 1-[3-(5,6,7,8-tetrahydronaphth-1-yloxy)-2-hydroxyprop-1-yl]-4-(2-acetaminophenyl)-piperazine dihydrochloride precipitates out; the yield was 76% of theory; m.p. 179°–183°C. (decomp.)

For the preparation of pharmaceutical compositions, the compounds (I) are mixed in the usual manner with solid or liquid pharmaceutical diluents or carriers and optionally also with odoriferous, flavoring and coloring materials and then shaped into, for example, tablets of dragees or, by the addition of appropriate adjuvants, suspended or dissolved in water or oil, for example in olive oil.

The compounds of the invention constitute potent antihypertensive agents. The compounds have proved particularly effective in the treatment of patients with severe or sustained elevation of blood pressure, particularly diastolic pressure. The compounds are suitable for use in almost all forms of fixed and progressive hypertensive disease, including that in which blood pressure is moderately elevated. The compounds have also proved effective in renal hypertension, including hypertension secondary to pyelonephritis, glomerulonephritis and renal amyloidosis.

The compounds can be administered orally, as pills, tablets, capsules, powders and the like. The preferred form of oral administration is as a tablet containing 1 to 20 mg of active compound.

The compounds can also be administered parenterally. Injection solutions containing 10 mg/ml of injection solution are preferred.

The dosage schedule is entirely dependent on the condition of the patient, his response to the treatment and whether or not he is ambulatory or hospitalized. The treatment should be begun with small doses (1 mg) and increased gradually depending upon the patient's response. The dosage can be increased at 5 to 7 day intervals until an average daily dose of 1 to 20 mg is reached. Only one dose a day is usually required.

In order to establish the effectiveness of the aminoguanidine compounds of the invention as agents for reducing blood pressure, a series of tests as follows were carried out.

The blood-pressure lowering action of the test compounds was determined in dogs 30 minutes after intravenous injection of 2.5 mg/kg of the compound. The animals were awake, and had been implanted with arterial and venous catheters for blood pressure recording or substance application and the blood pressure was measured 30 minutes after injection. The values set forth in the Table, below, are average values for two to six experiments per test compound.

The following compounds were used in the tests:

A. 4-(2-Chlorphenyl)-1-[3-(5,6,7,8-tetrahydronaphth-1-yl-oxy)-prop-1-yl]-piperazine B. 4-(2-Methylmercapto-phenyl)-1-[3-(5,6,7,8-tetrahydronaphth-1-yl-oxy)-prop-1-yl]-piperazine C. 4-(2-Methylphenyl)-1-[3-(5,6,7,8-tetrahydronaphth-1-yl-oxy)-prop-1-yl]-piperazine D. 1-[3-(5,6,7,8-Tetrahydronaphth-1-yl-oxy)-propyl]-4-phenylpiperazine E. 1-[3-(5,6,7,8-Tetrahydronaphth-1-yl-oxy)-propyl]-4-(2-methoxy-phenyl)piperazine F. 1-[3-(5,6,7,8-Tetrahydronaphth-1-yl-oxy)-2-hydroxy-prop-1-yl]-4-(2-methoxyphenyl)-piperazine G. 1-[3-(5,6,7,8-Tetrahydronaphth-1-yl-oxy)-2-hydroxy-prop-1-yl]-4-phenyl-piperazine H. 1-[3-(5,6,7,8-Tetrahydronaphth-1-yl-oxy)-2-hydroxy-prop-1-yl]-4-(2-methyl-phenyl)-piperazine I. 1-[3-(5,6,7,8-Tetrahydronaphth-1-yl-oxy)-2-hydroxy-prop-1-yl]-4-(2-chlorphenyl)-piperazine J. 1-[3-(5,6,7,8-Tetrahydronaphth-1-yl-oxy)-2-hydroxy-prop-1-yl]-4-(2-methylmercaptophenyl)-piperazine K. 1-[3-(5,6,7,8-Tetrahydronaphth-1-yl-oxy)-2-hydroxy-prop-1-yl]-4-(4-chlorphenyl)-piperazine The results of the experiment are set out in the Table which follows:

TABLE

| COMPOUND | BLOOD PRESSURE DECREASE DOSE IN MG/KG INTRAVENOUS INJECTION | MAXIMAL DECREASE IN AVERAGE ARTERIAL BLOOD PRESSURE IN mm Hg |
|---|---|---|
| A | 2.5 | 5 |
| B | 2.5 | 11 |
| C | 2.5 | 15 |
| D | 2.5 | 11 |
| E | 2.5 | 22 |
| F | 2.5 | 25 |
| G | 2.5 | 4 |
| H | 2.5 | 18 |
| I | 2.5 | 13 |
| J | 2.5 | 24 |
| K | 2.5 | 5 |
| 1-Phenyl-4-[3-(1-naphtyloxy)-2-hydroxy-propyl]-piperazine* (Comparison Compound) | 2.5 | ±0 |

*Pollard, C. B., J. Org. Chem. 23, 1935 (1958)

It will be understood that the specification and examples are illustrative but not limitative of the present invention and that other embodiments within the spirit and scope of the invention will suggest themselves to those skilled in the art.

What is claimed is:

1. 1-[3-(5,6,7,8-Tetrahydronaphth-1-yloxy)-propyl]-piperazine compound of the formula

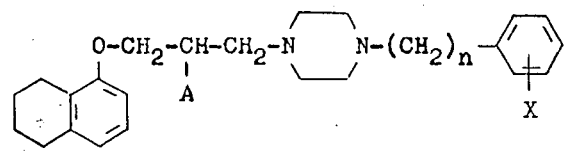

wherein
A is hydrogen or hydroxyl;
X is hydrogen, chlorine, alkyl, alkoxy, alkylthio, trifluoromethyl, nitro, amino or alkanoylamino; wherein the alkyl moieties in X contain up to 6 carbon atoms; and
$n$ is 0 or 1;
or the pharmacologically compatible acid addition salts thereof.

2. Compound as claimed in claim 1 wherein A is hydrogen.

3. Compound as claimed in claim 1 wherein A is hydroxyl.

4. Compound as claimed in claim 1 wherein X is hydrogen.

5. Compound as claimed in claim 1 wherein X is chlorine.

6. Compound as claimed in claim 1 wherein X is alkyl.

7. Compound as claimed in claim 1 wherein X is alkoxy or alkylthio.

8. Compound as claimed in claim 1 wherein X is trifluoromethyl, nitro or amino.

9. Compound as claimed in claim 1 wherein X is alkanoylamino.

10. Compound as claimed in claim 1 wherein $n$ is 0.

11. Compound as claimed in claim 1 wherein $n$ is 1.

12. Compound as claimed in claim 1 designated 4-(2-methylphenyl)-1-[3-(5,6,7,8-tetrahydronaphth-1-yloxy)-prop-1-yl]-piperazine.

13. Compound as claimed in claim 1 designated 1-[3-(5,6,7,8-tetrahydronaphth-1-yloxy)-propyl]-4-(2-methoxyphenyl)-piperazine.

14. Compound as claimed in claim 1 designated 1-[3-(5,6,7,8-tetrahydronaphth-1-yloxy)-2-hydroxyprop-1-yl]-4-(2-methoxyphenyl)-piperazine.

15. Compound as claimed in claim 1 designated 1-[3-(5,6,7,8-tetrahydronaphth-1-yloxy)-2-hydroxyprop-1-yl]-4-(2-methylphenyl)-piperazine.

16. Compound as claimed in claim 1 designated 1-[3-(5,6,7,8-tetrahydronaphth-1-yloxy)-2-hydroxyprop-1-yl]-4-(2-methylthiophenyl)-piperazine.

* * * * *